United States Patent [19]

Secor et al.

[11] Patent Number: 5,646,023

[45] Date of Patent: Jul. 8, 1997

[54] MODULATION OF SUGAR CONTENT IN PLANTS

[75] Inventors: Gary A. Secor; Alexander Y. Borovkov; Phillip E. McClean, all of Fargo; Joseph R. Sowokinos, Grand Forks, all of N. Dak.

[73] Assignees: J.R. Simplot Company, Boise, Id.; North Dakota State University of Agriculture and Applied Sciences, Bismarck, N. Dak.

[21] Appl. No.: 545,228

[22] Filed: Oct. 19, 1995

Related U.S. Application Data

[63] Continuation of Ser. No. 48,027, Apr. 15, 1993, abandoned.

[51] Int. Cl.$^6$ .............. C07H 21/04; C12N 15/29; C12N 15/82; A01H 5/00
[52] U.S. Cl. .............. 435/172.3; 536/23.6; 536/24.5; 800/205; 800/DIG. 42
[58] Field of Search .............. 800/205, DIG. 42; 536/23.6, 24.5; 435/172.3

[56] References Cited

FOREIGN PATENT DOCUMENTS

| | | |
|---|---|---|
| 0442592 | 8/1991 | European Pat. Off. . |
| 0530978 | 3/1993 | European Pat. Off. . |

OTHER PUBLICATIONS

Sowokinos, J., "Stress–Induced Alterations in Carbohydrate Metabolism," *Molecular & Cellular Biol.*, Chapter 11, pp. 137–158, CAB International (1990).

Nakano, K., et al., "UDP–Glucose Pyrophosphorylase from Potato Tuber: Purification and Characterization," *J. Biochem*, 106:528–532 (1989).

Katsube, T., et al., "UDP–Glucose Pyrophosphorylase from Potato Tuber: cDNA Cloning and Sequencing," *J. Biochem*, 108:321–326 (1990).

Manrow, R.E., et al., "Renaturation and localization of enzymes in polyacrylamide gels: Studies with UDPglucose pyrophosphorylase of Dictyostelium," *Proc. Natl. Acad. Sci. USA*, 77(2)730–734 (Feb. 1980).

Kimura, S., et al., "Purification, characterization and localization of rice UDP–glucose pyrophosphorylase," *Plant Physiol. Biochem.*, 30(6):683–693 (1992).

Haseloff, J., et al., "Simple RNA enzymes with new and highly specific endoribonuclease activities," *Nature*, 334:585–591 (18 Aug. 1988).

Müller–Röber, B., et al., "Inhibition of the ADP–glucose pyrophosphorylase in transgenic potatoes leads to sugar––storing tubers and influences tuber formation and expression of tuber storage protein genes," *The EMBO Journal*, 11(4):1229–1238 (1992). 4 Apr.

Stark et al 1992 (Oct. 9) Science 258:287–292.

von Schaewen et al 1990 The EMBO J. 9:3033–3044.

Worrell et al 1991 The Plant Cell 3:1121–1130.

Katsube et al 1991 Biochemistry 30:8546–8551.

Sonnewald et al 1992 (Aug.) Plant Physiol. 99:1267–1270.

*Primary Examiner*—Patricia R. Moody
*Attorney, Agent, or Firm*—Townsend and Townsend and Crew LLP

[57] ABSTRACT

The present invention provides novel transgenic plants with altered sugar levels and methods for producing them. The methods comprise introducing into the plant an expression cassette comprising a promoter sequence operably linked to a polynucleotide sequence substantially identical to a sequence from a gene encoding a protein associated with sucrose biosynthesis.

14 Claims, 3 Drawing Sheets

```
                              1052
POT
GENE      5'- A A A C C G G C C A G G T C G A A T C C A T C C A A -3'
RZ1052    3'- C A T G G G C C G G T C C A   C T T A G G T A G A T C -5'
             KpnI                       A C                  XbaI
                                        A  T G A T G A G T
                                        G                 C
                                         C A G G A G T G C
```

MODULATION OF SUGAR CONTENT IN PLANTS

This is a continuation of application Ser. No. 08/048,027, filed Apr. 15, 1993, now abandoned.

BACKGROUND OF THE INVENTION

This invention relates generally to the use of recombinant DNA methods for genetically altering plants. In particular, it relates to the modulation of the levels of sugars in plants using recombinant DNA.

Figure 1:
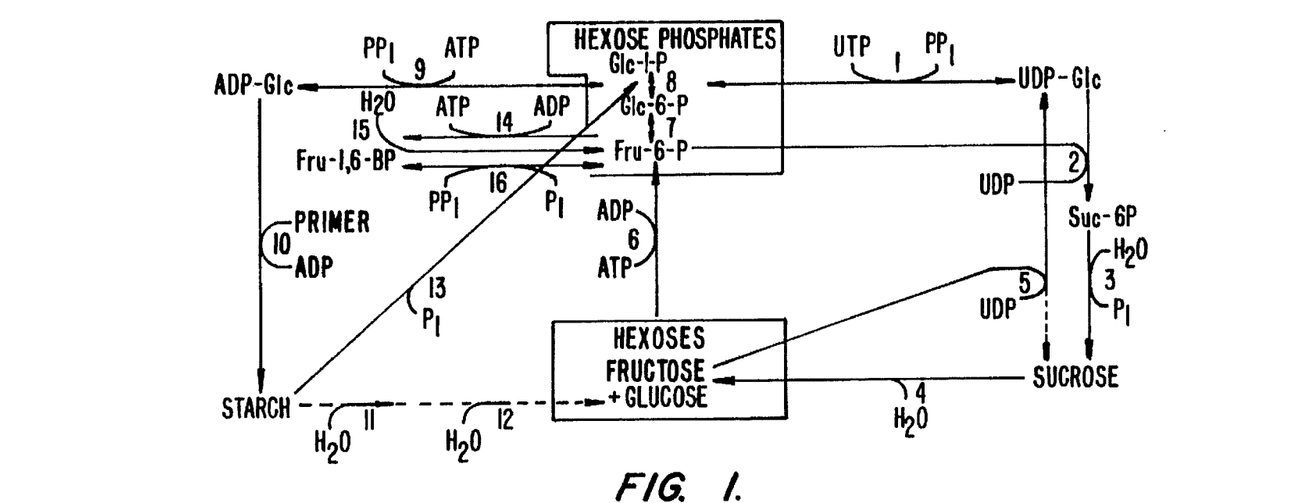

The growth and development of plants requires the products of the metabolic pathways that provide carbon. Two critical products of these pathways are sucrose and starch. UDP-glucose pyrophosphorylase (UGPase) (FIG. 1, reaction 1) is a key enzyme in the biosynthesis of both carbohydrates. Early in development the leaf is a sink, and the triose-phosphates that are the product of $CO_2$ fixation in the chloroplast are converted through a series of steps to the six carbon molecule glucose-1-phosphate. Through the action of ADP-glucose pyrophosphorylase (AGPase) (FIG. 1, reaction 9), this molecule is converted to ADP-glucose which is the primary substrate for starch biosynthesis. As the leaf matures it becomes a source of carbon for the growth of other tissues, and the metabolism switches to sucrose biosynthesis. At this point, the triose phosphates are transported to the cytoplasm and are converted to glucose-1-phosphate by the same reactions that occur in the chloroplast. The glucose-1-phosphate is then converted by UGPase to UDP-glucose which is a substrate for sucrose biosynthesis (FIG. 1, reactions 2 and 3). Xu et al. *Plant Physiol.* 90:635–642 (1989).

UGPase activity is also associated with non-photosynthetic sink tissues such as the potato tuber. When sucrose is delivered to sink tissues, it is cleaved by sucrose synthase (SS) (FIG. 1, reaction 5) to UDP-glucose and fructose. UGPase then converts the UDP-glucose to glucose-1-phosphate. At this point, the hexose phosphate enters the amyloplast and serves as substrate for AGPase, and subsequently starch synthesis. Under stress conditions, starch is degraded and glucose-1-phosphate is released from the amyloplast and can then enter the same cytoplasmic sucrose biosynthetic pathway involving UGPase described above.

Regulation of the interconversion of starch and sugars is of significant commercial interest. For instance, starch breakdown in the tuber is an important consideration to the potato industry. During cold storage, the reducing sugars glucose and fructose accumulate after starch degradation. The hexose accumulation begins when glucose-1-phosphate is released during starch degradation (FIG. 1, reaction 13). As in the leaf cytoplasm, the glucose-1-phosphate is converted to sucrose by UGPase, sucrose phosphate synthase (SPS), and sucrose-6-phosphate phosphatase. Hexoses are then formed when invertase cleaves sucrose into its hexose sugar components (FIG. 1, reaction 4).

The accumulation of hexose sugars leads to a darkening of chips or fries during cooking as a result of a non-enzymatic Maillard reaction which involves a condensation between the free sugar aldehydes and the amine groups of amino acids. Thus, methods of controlling the expression of the genes in these metabolic pathways could lead to improved commercial varieties of potatoes and other plants.

One potential method of controlling plant gene expression is the use of ribozymes. Only circumstantial evidence of the activity of ribozymes in plants has been reported in literature. The self-splicing of *Chlamydomonas reinhardtii* chloroplast ribosomal RNA was the first evidence of autocatalytic RNA activity in plant kingdom. Durrenberger et al., *EMBO J.* 10:3495–3501 (1991). Recently a specific activity of a hammerhead-type ribozyme has been shown in *Nicotiana tabacum* protoplasts (Steinecke et al., 1992). No report of the ability of ribozymes to produce a phenotypic change in transgenic plants has been shown, however.

A need exists to identify economical methods for controlling metabolic pathways associated with starch synthesis. In particular, new methods of inhibiting gene expression (e.g., by ribozymes) in transgenic plants would provide new techniques for modifying a number of plant traits.

SUMMARY OF THE INVENTION

The present invention provides methods for modulating the levels of sugars in plants, usually a member of the genus *Solanum*, using recombinant DNA techniques. The methods involve introducing into the plant an expression cassette comprising a promoter sequence operably linked to a polynucleotide from a gene encoding a protein associated with sucrose biosynthesis. Preferably, the enzyme is potato UDP-glucose pyrophosphorylase and the plant is *Solanum tuberosum*.

The polynucleotide can be linked to the promoter in an antisense orientation. Alternatively the polynucleotide sequence is a ribozyme sequence. The polynucleotide sequence may consist of between about 50 and about 2000 basepairs. In a preferred embodiment, the sequence will comprise 1.2 kb from the gene.

The expression cassette can be introduced into the plant using in vitro techniques (e.g. using *Agrobacterium*) or by a sexual cross. The promoter may be constitutive (e.g., the 35S promoter of cauliflower mosaic virus) or inducible.

The invention also provides plants (e.g., *Solanum tuberosum*) comprising an expression cassette in which a promoter sequence is operably linked to the polynucleotide sequence described above. The polynucleotide sequence may be linked to the promoter sequence in an antisense orientation or may be a ribozyme sequence.

The invention further provides methods of inhibiting the accumulation of sugars in a tuber. The methods comprise introducing into a tuber-producing plant an expression cassette comprising a promoter sequence operably linked to a polynucleotide sequence from a gene encoding UDP-glucose pyrophosphorylase. The expression cassette can be introduced into the plant using *Agrobacterium* or by a sexual cross.

DEFINITIONS

The phrases "polynucleotide sequence" or "nucleic acid segment" refer to a single or double-stranded polymer of deoxyribonucleotide or ribonucleotide bases read from the 5' to the 3' end. It includes both self-replicating plasmids, infectious polymers of DNA or RNA and non-functional DNA or RNA.

The term "promoter" refers to a region of DNA upstream from the structural gene and involved in recognition and binding RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid. Plants from the genus Solanum are preferably used.

The term "expression" refers to the transcription and translation of a structural gene so that a protein is synthesized.

A "constitutive" promoter is a promoter which is active under most environmental conditions and states of development or cell differentiation.

An "inducible" promoter is a promoter which is under more precise environmental or developmental control. Examples of environmental conditions that may effect transcription by inducible promoters include anaerobic conditions or the presence of light. Examples of promoters under developmental control include promoters that initiate transcription only in certain tissues, such as root specific promoters.

The term "antisense orientation" refers to the orientation of nucleic acid sequence from a structural gene that is inserted in an expression cassette in an inverted manner with respect to its naturally occurring orientation. When the sequence is double stranded, the strand that is the template strand in the naturally occurring orientation becomes the coding strand, and vice versa.

The term "uninterrupted" refers to a DNA sequence (e.g., cDNA) containing an open reading frame that lacks intervening, untranslated sequences.

The term "operably linked" refers to functional linkage between a promoter and a second sequence, wherein the promoter sequence initiates transcription of RNA corresponding to the second sequence.

The term "reducing sugar" refers to a monosaccharide or disaccharide having free aldehyde or carbonyl groups and capable of reducing copper or silver salts in alkaline solutions, for example Fehling's solution.

A "ribozyme sequence" is a catalytic RNA sequence capable of cleaving a target RNA. The term also encompasses a DNA sequence in an expression cassette from which the RNA is transcribed.

BRIEF DESCRIPTION OF THE DRAWINGS

FIG. 1 shows the metabolic pathways involved in starch and sucrose synthesis and degradation. The enzymes that perform the reactions are as follows: 1) UTDP-glucose pyrophosphorylase (UGPase); 2) sucrose-6-phosphate synthase (SPS); 3) sucrose-6-phosphate phosphatase, 4) invertase; 5) sucrose synthase (SS); 6) hexokinase; 7) phosphohexoseisomerase; 8) phosphoglucomutase; 9) ADP-glucose pyrophosphorylase (AGPase); 10) starch synthase; 11) amyloglucosidase and debranching enzyme; 12) amylase; 13) starch phosphorylase; 14) ATP-phosphofructokinase; 15) fructose-1,6-bisphosphatase; 16) PPi-phosphofructokinase.

FIG. 4 shows the results of an in vitro ribozyme assay. Lane 1—Antisense UGPase RNA incubated with antisense RZ1052 RNA. Lane 2—Sense UGPase RNA incubated with antisense RZ1052 RNA. Lane 3—Antisense UGPase RNA incubated with sense RZ1052 RNA. Lane 4—Sense UGPase RNA incubated with sense RZ1052 RNA. Arrow shows the ≈1.0. kb of ribozyme cleavage.

DESCRIPTION OF THE PREFERRED EMBODIMENTS

The metabolic pathway presented in Equation 1, below, is fragment of the metabolic pathways shown in FIG. 1. In particular, it shows the enzymes associated with the biosynthesis and utilization of sucrose.

EQUATION 1

1—UDP-glucose pyrophosphorylase (UGPase, EC 2.7.7.9)
2—sucrose synthase (SS, EC 2.4.1.13 )
3—sucrose-6-phosphate synthase (SPS, EC 2.3.1.14)
4—sucrose-6-phosphate phosphatase (SPP, EC 3.1.3.24)
5—alkaline and acid invertases (INV, EC 3.2.1.26)

The enzymes associated with the sucrose biosynthetic pathway (i.e., enzymes 1–5) are particularly good targets for the regulation of starch/sugar interconversion and the accumulation of reducing sugars. For instance, the irreversible reaction catalyzed by alkaline and acid invertases can be suppressed without interfering with synthesis of sucrose during vegetative growth of the plant. The presence of a number of different invertases has been shown in different tissues. Davies et al. *J. Cell. Biochem., Suppl.* 16F:224 (1992).

Sucrose synthase has been shown to catalyze the conversion of sucrose and UDP to fructose and UDP-glucose in plant cells. Huber et al., *Plant Physiol.* 81:1008–1013 (1986). Although the enzyme catalyzes a reversible reaction, its primary role is apparently in sucrose utilization for respiration or starch biosynthesis.

The synthesis of sucrose is primarily controlled by sucrose-6-phosphate synthase and sucrose-6-phosphate phosphatase. Down regulation of either of these enzymes can be conveniently used to prevent accumulation of sugars.

As noted above, UDP-glucose is formed from glucose-1-phosphate and UTP by the action of UGPase. The metabolic importance of the enzyme in the direction of UDP-glucose formation is particularly evident in mutant strains of *Dictyostelium* that have reduced UGPase activity. The morphogenesis of the mutant strains is arrested in stages of growth that require stored glycogen to be mobilized for use in cellulose formation. Dimond et al., *Dev. Biol.* 50:169–181 (1976).

In the tuber, SPS requires a 10-fold higher concentrations of UDP-glucose than in the leaf (Murata 1972). Among potato cultivars, genetic variation has been demonstrated for the cold-induced increase in the level of these hexoses (Sowokinos, *Amer Potato J.* 64:459–460 (1987). In addition, the level of the free hexoses in the tuber following cold storage is correlated with UGPase activity. Sowokinos in *Molecular and Cellular Biology of the Potato*, pp 137–158, Vadya and Park, eds., (C.A.B. International, Wallingford, U.K. 1990), which is incorporated herein by reference. Plants with low UGPase activity have been found to accumulate lower levels of reducing sugars. UGPase from potato tubers has been isolated and partially characterized by Nakano et al., *J. Biochem.* 106:528–532 (1989), which is incorporated herein by reference.

A number of strategies can be used to alter the activity of any of the enzymes noted above. In the embodiments illustrated below, sugar levels are decreased by inhibiting the activity of UGPase. The present invention provides methods that can be used to increase or decrease sugar levels in a number of commercially important plants, in particular, tuber-producing plants. The most common commercially important tuber-producing plants include, potato (*Solanum*

*tuberosum*), yam (*Dioscorea batatas*), sweet potato (*Ipomoea batatas*), and the like. Other plants in which sugar levels can be modulated, typically by increasing sucrose content, include tomatoes, strawberries, apples, oranges, sugar beet, corn, and the like.

If decreased sucrose accumulation is desired, activity of one of the enzymes noted above is suppressed. The metabolic steps catalyzed by an enzyme can be blocked using, for instance, antisense regulation of the gene encoding the enzyme associated with that step. To accomplish this, a polynucleotide sequence from the desired gene (e.g., UGPase) is cloned and operably linked to a promoter such that the antisense strand of RNA will be transcribed. The construct is then transformed into plants and the anti-sense strand of RNA is produced. In plant cells, it has been shown that anti-sense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801, 340 which are incorporated herein by reference.

Introduction of cloned polynucleotide sequences configured such that the sense-strand of RNA is produced is also an effective means by which to block the transcription of target genes. For an example of the use of this method to modulate expression of endogenous genes see, Napoli et al., *The Plant Cell* 2:279–289 (1990), and U.S. Pat. No. 5,034, 323, which are incorporated herein by reference.

A third approach is the use of catalytic RNA molecules or ribozymes. It is possible to design ribozymes which can specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus.

Analysis of the self-cleaving RNAs reveals the presence of a conserved regions necessary for cleavage and allows the design of ribozymes specific for a target RNA. The design and use of target RNA-specific ribozymes is described in Haseloff et al. *Nature*, 334:585–591 (1988), which is incorporated herein by reference.

First, a specific site for cleavage must be identified within the target RNA. In naturally occurring cleavage sites, the sequence, GUC, usually immediately precedes the site. Cleavage is also possible after the sequences GUA, GUU, CUC, AUC and UUC, as well. Potential cleavage sites within the target RNA can be identified using these sequences.

Next, the catalytic region of the ribozyme comprises certain sequences that are highly conserved in naturally occurring cleavage domains. Conserved tertiary folding in this region appears to be important to the activity of the ribozyme.

Finally, the catalytic region and the RNA substrate are held together by flanking regions of base pairing between the RNA substrate and the ribozyme. The base pairing must allow accurate positioning of the catalytic region relative to the cleavage site on the RNA substrate. The extent and type of pairing will directly affect the specificity of the ribozyme. The selection of these sequences will obviously depend upon the target RNA substrate.

Using the design considerations described above, DNA sequences capable of transcribing the appropriate ribozyme, which specifically binds and cleaves the target RNA can be synthesized. Using standard techniques as described in detail below, the DNA sequences are operably linked to a plant promoter and introduced into a plant, where they inhibit the expression of the target gene. The sequence which transcribes the ribozyme will include two parts: one part encodes the catalytic region which is usually between about 15 and about 40 base pairs, usually 24 base pairs; and a second part encodes the flanking regions which each can be as few as 6 base pairs in length but can be between about 20 and about 100 base pairs, usually between about 30 and about 70 base pairs.

I. General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989), which is incorporated herein by reference.

In summary, preparation of polynucleotide sequences from gene associated with sucrose biosynthesis (e.g., the gene encoding UGPase) suitable for use in the present invention and introduce them into a plant cell involve some or all of the following steps: 1) purifying desired enzymes from the appropriate sources, 2) preparing oligonucleotide probes corresponding to a portion of the amino acid sequence of the purified enzymes, 3) screening a cDNA or genomic library for the sequences which hybridize to the probes, 4) linking a plant promoter and other sequences necessary for expression to the identified sequences (the sequences can be linked in the antisense or sense direction), 5) transforming suitable host plant cells, and 6) selecting and regenerating cells which transcribe the sequences and display altered sugar levels.

II. Purification of Enzymes and Synthesis of Oligonucleotide Probes

Methods for purifying desired proteins are well known in the art and are not presented in detail here. For a review of standard techniques see, *Methods in Enzymology*, "Guide to Protein Purification", M. Deutscher, ed. Vol. 182 (1990), which is incorporated herein by reference. For example, UGPase can be purified according to the methods described in Nakano et al., above. The enzyme is isolated from crude extracts using standard purification techniques such as ammonium sulfate precipitation and dialysis. Further purification of the extract typically includes conventional chromatographic procedures such as ion exchange (e.g., DEAE), dye affinity, hydroxylapatite, and ligand affinity chromatography. It is typically purified to the point that it can be identified as a distinct band by polyacrylamide gel electrophoresis (PAGE).

The enzyme is then assayed for its activity using standard techniques. For instance, assays suitable for detecting UGPase activity are disclosed in Nakano et al. supra. In addition, UGPase activity is determined by the one step spectrophotometric method of Sowokinos, *Plant Physiol.* 57: 63–68 (1976), which is incorporated herein by reference.

After isolation of the enzyme, the amino acid sequence of the N-terminus is determined and an oligonucleotide probe, designed to hybridize to the desired gene, is synthesized. Amino acid sequencing is performed according to standard techniques (see, e.g., Matsudaira *J. Biol. Chem.* 262:10035–10038 (1987), which is incorporated herein by reference. Oligonucleotide probes are synthesized according to standard techniques as described, for instance, in Sambrook et al., supra.

Oligonucleotide probes useful for identification of desired genes can also be prepared from conserved regions of related genes in other species. For instance, probes derived from a gene encoding a UGPase from potato may be used to screen libraries prepared from other plants.

III. Preparation of Libraries for Screening

Genomic or cDNA libraries are prepared according to standard techniques as described, for instance, in Sambrook, supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids. Vectors particularly useful in the present invention include EMBL 3 and 4, Lambda Zap (Stratagene).

Alternatively, cDNA libraries can be used to screen for the desired gene. To prepare cDNA from various genes involved in starch/sugar interconversion, mRNA from a suitable source, for instance potato tubers, is first isolated. Eukaryotic mRNA has at its 3' end a string of adenine nucleotide residues known as the poly-A tail. Short chains of oligo d-T nucleotides are then hybridized with the poly-A tails and serve as a primer for the enzyme, reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or λ phage vector for propagation in *E. coli*.

Identification of clones harboring the desired polynucleotide sequences is performed by either nucleic acid hybridization or immunological detection of the encoded protein, if an expression vector is used. The bacterial colonies are then replica plated on nitrocellulose filters. The cells are lysed and probed with either oligonucleotide probes described above or with antibodies to the desired protein.

IV. Vector Construction

Selection of an appropriate vector useful in the present invention is relatively simple, as the constraints are minimal. The minimal requirements of the vector are that the desired nucleic acid sequence be introduced in a relatively intact state. Thus, any vector which will produce a plant carrying the introduced DNA sequence should be sufficient. Any vector which will introduce a substantially intact RNA which can ultimately be converted into a stably maintained DNA sequence is also acceptable.

Even a naked piece of DNA would be expected to be able to confer the properties of this invention, though at low efficiency. The decision as to whether to use a vector, or which vector to use, will be guided by the method of transformation selected. This determination is considered to be well with in the ordinary skill of those in the art.

The vectors useful in the present invention include, but are not limited to, the Ti plasmid vectors and shuttle vectors designed for particle gun transformation. The selection of vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press, incorporated herein by reference).

The vectors typically comprise additional attached sequences which confer resistance to degradation of the nucleic acid fragment, which assist in the process of genomic integration, or which provide a means to easily select for those cells or plants which are transformed. Such sequences are advantageous and greatly decrease the difficulty of selecting useable transformed plants.

The recombinant vectors of the present invention typically comprise an expression cassette designed for initiating transcription of the desired polynucleotide sequences in plants. Companion sequences, of bacterial origin, are also included to allow the vector to be cloned in a bacterial host. The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

For expression in plants, the recombinant expression cassette will contain, in addition to the desired polynucleotide sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the transcription start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Other sequences conferring tissue specificity, response to environmental signals, or maximum efficiency of transcription may also be found in the promoter region. Such sequences are often found within 400 bp of transcription start site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of premoters which direct transcription in plant cells is suitable. The promoter can be either constitutive or inducible. Promoters of bacterial origin include the octopine synthase promoter, the nopaline synthase promoter and other promoters derived from native Ti plasmids. Herrara-Estrella et al., *Nature*, 303:209–213, 1983. Viral promoters include the 35S and 19S RNA promoters of cauliflower mosaic virus. Odell et al. *Nature*, 313:810–812, 1985. Possible plant promoters include the ribulose-1,3-bisphosphate carboxylase small subunit promoter and the phaseolin promoter.

A promoter which is expressed concurrently with or prior to the normal activation of the homologous endogenous sequence is generally preferred. A constitutive promoter is most preferred, such as the cauliflower mosaic virus promoter. This promoter is constitutive because its operation is relatively independent of the developmental stage of the cell in which it is contained.

A regulated or inducible promoter, such as ones associated with the ribulose-1,5-bisphosphate carboxylase, the chlorophyll binding proteins or the glycine-rich root protein genes are also suitable. Control may be either temporal with respect to the developmental stage of the cell, or spatial with respect to different parts or organs of the plant. The operation of a promoter may also vary depending on its location in the genome. Thus, an inducible promoter may become fully or partially constitutive in certain locations. Promoters particularly useful in the present invention include tuber specific promoters such as the promoter for the gene encoding the tuber protein patatin.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419–434, 1982. Polyadenylation sequences include, but are not limited to the *Agrobacterium* octopine synthase signal (Gielen et al., *EMBO J.*, 3:835–846, 1984) or the nopaline synthase signal (Depicker et al., *Mol. and Appl. Genet*, 1:561–573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

Other features of the vectors of the present invention include various 5' untranslated leader sequences such as the "cab leader" from petunia or the "omega leader" from tobacco mosaic virus.

In the present invention the polynucleotide sequence to be introduced using the vectors described above is a "polynucleotide sequence from a gene encoding a protein associated with sucrose biosynthesis". This term as defined here refers to a sub-sequence or full length polynucleotide sequence of a gene, such as the UGPase gene, which, when present in a transgenic plant has the desired effect, for example, inhibiting expression of the endogenous UGPase gene. In the case of both expression of transgenes and inhibition of endogenous genes (e.g., by antisense, ribozymes or sense suppression) one of skill will recognize that the inserted polynucleotide sequence need not be perfectly identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term specifically includes those full length sequences that encode a polypeptide having at least 95% identity (determined as described below) with the source protein and that retain the function of the source protein. Thus, in the case of UGPase, the above term includes variant polynucleotide sequences encoding polypeptides which have at least 95% identity with the amino acid sequence of potato UGPase and which have UGPase activity which can be detected in the assays described below.

In the case of polynucleotides used to inhibit expression of an endogenous gene, the introduced sequence also need not be perfectly identical to a sequence of the target. The introduced polynucleotide sequence will typically be at least substantially identical (as determined below) to the target endogenous sequence.

Thus, vectors can be designed such that the inhibitory effect applies to other proteins within a family of genes exhibiting substantial identity to the target gene. For example, UGPase may be encoded by one or more homologous genes which comprise a gene family. Thus, repression of one member of the family will typically serve to impose the same repressive effect on others of the family. Similarly, segments from UGPase genes from other plant species may be utilized.

The introduced sequence also need not be full length relative to either the primary transcription product or fully processed mRNA. A higher sequence identity in a shorter than full length sequence compensates for a longer less identical sequence. Furthermore, the introduced sequence need not have the same intron or exon pattern, and identity of non-coding segments will be equally effective. Normally, a sequence of between about 10 nucleotides and 2000 nucleotides should be used, though a sequence of between about 100 and about 1500 nucleotides is preferred, and a sequence of between about 500 and about 1200 nucleotides or a full length gene is especially preferred.

Two nucleic acid sequences or polypeptides are said to be "identical" if the sequence of nucleotides or amino acid residues in the two sequences is the same when aligned for maximum correspondence as described below. The term "complementary to" is used herein to mean that the complementary sequence is homologous to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

"Percentage of sequence identity" is determined by comparing two optimally aligned sequences over a window of comparison of 20 positions, wherein the portion of the polynucleotide sequence in the comparison window may comprise additions or deletions (i.e., gaps) of 20 percent or less, usually 5 to 15 percent, or 10 to 12 percent, as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity.

The term "substantial identity" means that a polynucleotide or polypeptide comprises a sequence that has at least 80% sequence identity, preferably 95% or more, compared to a reference sequence over a comparison window, allowing for gaps in the sequence as described above.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

V. Transcription of the Desired Polynucleotide Sequence in Plant Cells

A. Transformation of plant cells by in vitro techniques

1. Direct Transformation

The vectors described above can be microinjected directly into plant cells by use of micropipettes to mechanically transfer the recombinant DNA. Crossway, *Mol. Gen. Genetics*, 202:179–185 (1985). The genetic material may also be transferred into the plant cell using polyethylene glycol, Krens, et al., *Nature*, 296:72–74 (1982).

Another method of introduction of polynucleotide sequences is particle acceleration of small particles with the nucleic acid either within the matrix of small beads or particles, or on the surface, Klein, et al., *Nature*, 327:70–73 (1987).

Yet another method of introduction is fusion of protoplasts with other entities, either minicells, cells, lysosomes or other fusible lipid-surfaced bodies. Fraley, et al., *Proc. Natl. Acad. Sci. USA*, 79:1859–1863 (1982).

The DNA may also be introduced into the plant cells by electroporation. Fromm et al., *Proc. Natl Acad. Sci. USA*, 82:5824 (1985). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

2. Vectored Transformation

Cauliflower mosaic virus (CaMV) may be used as a vector for introducing the anti-sense DNA into plant cells. (Hohn et al., 1982 "Molecular Biology of Plant Tumors," Academic Press, New York, pp.549–560; Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

A preferred method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Preferred *Agrobacterium* strains useful in the present invention include LBA 4404, C58C1, EHA 101, W2/73, R1601, LBA 288, GV 3850, A281, GV311 SE, A856, A136, GC3101, 1S955, and bo 42.

*Agrobacterium* is a genus in the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. J. Schell, *Science*, 237:1176–1183 (1987).

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid, such vectors are typically termed binary vectors. Hoekema, et al., *Nature*, 303:179–189 (1983). The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkun and Ausubel, 1981, Nature 298:85–88), promoters, (Lawton et al., 1987, Plant Mol. Biol. 9:315–324) and structural genes for antibiotic resistance as a selection factor (Fraley et al., Proc. Nat. Acad. Sci. USA, 80:4803–4807, 1983).

All plant cells which can be transformed by *Agrobacterium* and from which whole plants can be regenerated can be transformed according to the present invention to produce transformed intact plants which contain the desired DNA. There are two common ways to transform plant cells with *Agrobacterium:*

(1) co-cultivation of Agrobacterium with cultured isolated protoplasts, or (2) transformation of intact cells or tissues with *Agrobacterium*.

Method (1) requires an established culture system that allows for culturing protoplasts and subsequent plant regeneration from cultured protoplasts.

Method (2) requires (a) that the intact plant tissues, such as cotyledons, can be transformed by *Agrobacterium* and (b) that the transformed cells or tissues can be induced to regenerate into whole plants.

Most dicot species can be transformed by *Agrobacterium*. All species which are a natural plant host for *Agrobacterium* are transformable in vitro. Monocotyledonous plants, and in particular, cereals, are not natural hosts to *Agrobacterium*. There is growing evidence now that certain monocots can be transformed by Agrobacterium. Using novel experimental approaches cereal species such as rye (de la Pena et al., *Nature* 325:274–276, 1987), corn (Rhodes et al., *Science* 240:204–207, 1988), and rice (Shimamoto et al., *Nature* 338:274–276, 1989) may now be transformed, see also, HooykasVan Slogteren et al., *Nature*, 311:763–764 (1984).

B. Selection and Regeneration of Transformed Plant Cells

After transformation, transformed plant cells or plants comprising the introduced DNA must be identified. A selectable marker, such as those discussed, supra, is typically used. Transformed plant cells can be selected by growing the cells on growth medium containing the appropriate antibiotic. The presence of opines can also be used if the plants are transformed with *Agrobacterium*.

After selecting the transformed cells, one can confirm expression of the desired heterologous gene. Simple detection of mRNA encoded by the inserted DNA can be achieved by well known methods in the art, such as Northern blot hybridization. The inserted sequence can be identified using the polymerase chain reaction (PCR) and Southern blot hybridization, as well. See, e.g., Sambrook, supra.

After determination of the presence of the DNA, whole plant regeneration is desired. All plants from which protoplasts can be isolated and cultured to give whole regenerated plants can be hosts for the polynucleotide sequences of the present invention. Some suitable plants in which sugar starch metabolism may be controlled include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Cichorium, Helianthus, Lactuca, Bromus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, Phaseolus, Pisum, Hordeum, Beta* and *Datura*.

As discussed above, tuber-producing plants such as potatoes, yams, and sweet potato are particularly preferred.

Plant regeneration from cultured protoplasts is described in Evans et al., *Handbook of Plant Cell Cultures*, Vol. 1: (MacMillan Publishing Co. New York, 1983); and Vasil I.R. (ed.), *Cell Culture and Somatic Cell Genetics of Plants*, Acad. Press, Orlando, Vol. 1, 1984, and Vol. III, 1986.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Regenerated plants with the desired characteristics are typically identified by determining activity of the target enzyme. For instance, UGPase activity can be determined using the methods disclosed in Sowokinos (1976), supra.

To identify phenotypic changes, the levels of sugars, e.g. glucose and fructose, in the plants can be measured. Typically, the level of reducing sugars in tubers is determined using, for instance, a glucose analyzer such as the Yellow Springs Instruments (YSI) industrial analyzer.

While many of the improvements suggested above are not essential, the efficiency of production of useful transformants may be significantly affected. Some of the transformants may be identical to the parental plants, others may have altered reducing sugar levels in the tubers or other organs of interest. Others may have altered levels in certain cells or patches of cells resulting in regular or irregular patterns. Tubers on the same plant may even have different patterns. The likelihood of obtaining a desirable transformant will depend upon the number of plants screened and the efficiency of actual transformation and expression of the foreign nucleic acid sequence. In addition, a number of factors may affect expression of the introduced polynucleotide sequence, including the type of promoter, the temporal pattern of the promoter, and the site of incorporation within the genome.

If the introduced polynucleotide sequence is an intact gene from the target plant or other plant species (meaning a complete gene containing coding sequences, intron, promoter, enhancers and other cis-acting regulatory elements either upstream (5') or downstream (3') of the coding sequences), a fraction of independent transformed plants, may carry the introduced gene in locations that result in abnormal expression. If the introduced gene is a chimeric gene (meaning that one or more elements, such as a promoter, from another gene has been substituted) and is driven by a constitutive promoter, then abnormal levels and times of expression will be achieved in a large fraction of the transformed plants. If the introduced gene is a chimeric gene and is driven by a developmentally regulated promoter, depending on the promoter, some fraction of plants will show abnormal levels and times of expression of the introduced gene.

Finally, one of skill will recognize that after the expression cassette is stably incorporated in transgenic plants and confirmed to be operable, it can be introduced into other plants by sexual crossing. Any of a number of standard breeding techniques can be used, depending upon the species to be crossed.

The following examples illustrate, but do not limit, the invention.

EXAMPLE 1

Isolation, Cloning and Sequencing of the Potato UGPase Gene

A 1.2 kb PstI fragment containing approximately the last third of the coding region of UGPase was generated from a PCR amplification product of potato DNA obtained using UGPase-specific primers. The primers were designated 37B and 37AM and had the following sequences:

```
         W   Y   P   P   G   H   G (Seq. ID NO.:1)
37B  5'-TGG TAT CCI CCI GGI CAT GG-3' (Seq. I.D. NO.:2)
             C           C
         T   G   D   V   W   F   G (Seq. ID No.:3)
37AM 5'- TGI CCI CTA CAI ACC AAA CC-5' (Seq. I.D. NO:4)
                                 G
```

The sequence of the primers was based on the amino acid sequence disclosed in Nakano et al., supra. The product of the reaction is a single 2.5 Kb fragment of DNA:

The internal PstI fragment was cloned in pUC19 (plasmid named pUC19-pot-Pst-1.2).

EXAMPLE 2

Construction of Antisense and Ribozyme Vectors

Figure 2:
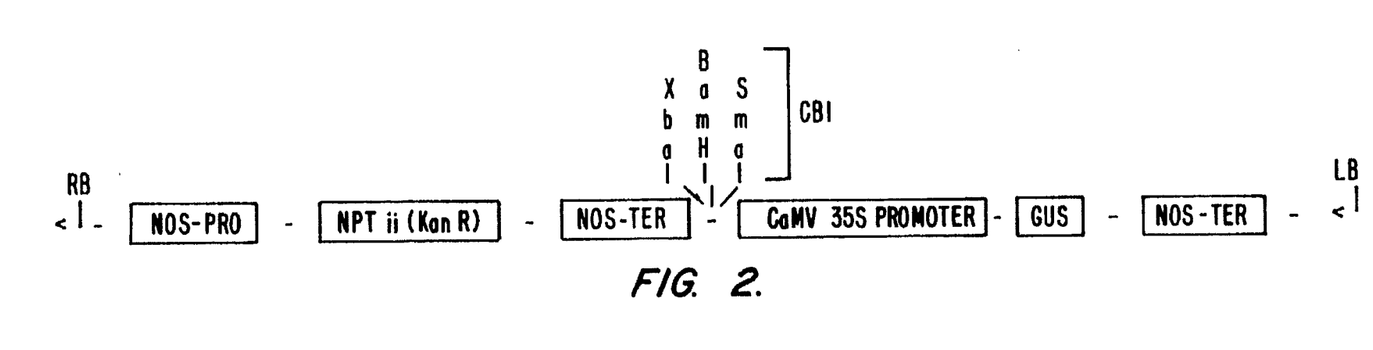
FIG. 2 is a diagram of the vector pBI121.

The disarmed Ti plasmid vector pBI121 which was carried in *Agrobacterium tumefaciens* LBA 4404 (received from Dr. William Belnap, USDA-ARS-WRRC, Albany, Calif.) was used for the transformations. The vector is described in Jefferson, et al., *EMBO J.* 6:3901–3907 (1987), which is incorporated herein by reference. A map of pBI121 is shown in FIG. 2. The plasmid contains the CaMV 35S promotor upstream from the betaglucuronidase (GUS) gene. Between the promotor and the GUS genes is located the sequence TCTAGAGGATCCCCGGG (Seq. ID No.: 5) which contains 3 unique restriction sites, XbqaI, BamHI and SmaI very close to each other.

The fragment of the UGPase gene was released from the pUC19-pot-Pst-1.2 plasmid as a BamHI-SphI fragment. The SphI end was blunt ended with Klenow and the resultant fragment subcloned into the BamHI-SmaI site of pBI121.

The resulting plasmid carried the fragment of the UGPase gene in antisense orientation under the control of the CaMV 35S promotor.

Figure 3:
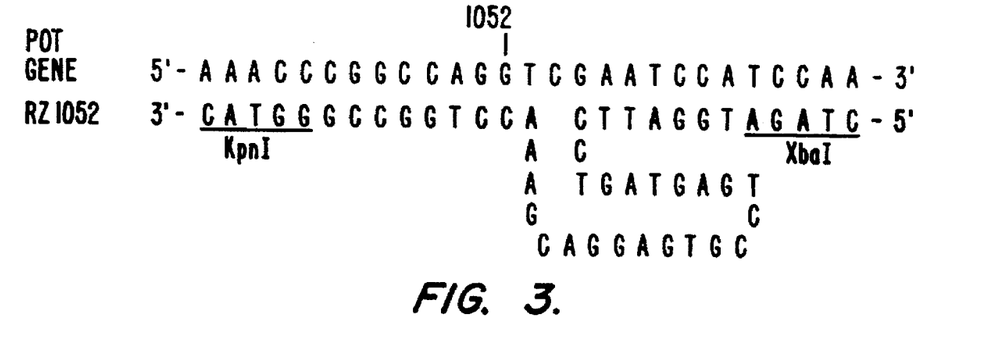
FIG. 3 shows the sequence of the ribozyme 1052 and the target sequence in the UGPase gene (SEQ ID. NOS. 6 and 7).

The sequence of the 1.2 kb PstI fragment was used to design a ribozyme specific to UGPase mRNA. Only two potential ribozyme cleavage sites were found in the coding region of the fragment, and a ribozyme (RZ1052) was designed for one site (FIG. 3).

To prepare the vector comprising the ribozyme 1052(92), the ribozymes was cloned in pGEM4Z (Promega, Madison, Wisconson) between the KpnI and the XbaI sites. The recombinant plasmid named pGEM4Z-RZ92 contains KpnI, XbaI and all of the rest of the sites from the multiple cloning region except SmaI and BamHI. The construction and sequence of pGEM4Z-RZ92 was checked by restriction analysis and sequencing.

The ribozyme sequence was released from pGEM4Z-RZ92 with XbaI-EcoRI. The EcoRI was blunt ended with Klenow and the resultant fragment subcloned into the XbaI-SmaI site of pBI121. pBI121-RZ92 contains the ribozyme sequence 1052(92) downstream from the CaMV 35S promotor and produces active ribozyme under the control of the CaMV 35S promotor.

The ribozyme was cloned and tested in vitro. Normally linearized plasmids are used to make the RNA transcripts. But because the cleavage site (nucleotide 1052) is located near the 3' end of the transcript, it is difficult to distinguish a 1134 nt full transcript from a 1052 nt cleavage product in either agarose or acrylamide gels. To overcome this problem the circular plasmid was transcribed. Cleavage of the transcriptional product with an active ribozyme generated a prominent 1052 nt product derived from the 5' end of the transcription products of the circular plasmid. This fragment was distinct from higher molecular weight fragments that were not cleaved by the ribozyme. The specificity of the ribozyme was tested against sense and antisense transcripts of the 1.2 kb fragment.

Testing ribozyme activity was performed as follows. RZ1052 and the 1.2 kb Pstl fragment of UGPase gene were cloned in the sense and antisense orientations downstream of the T7 RNA polymerase promoter in the vector pGEM4Z. Radioactive RNAs were transcribed in vitro by T7 RNA polymerase from both strands of the 1.2 kb Pstl fragment of the UGPase gene cloned in pGEM4Z by the procedure described in the Promega Protocols and Application Guide (Promega Corporation). The same procedure was used to transcribe non-radioactive ribozyme transcripts from the sequence cloned in pGEM4Z. Substrate and ribozyme RNAs were incubated in a molar ratio of 1:2 in 50 MM Tris-HCl (pH 8.0), 20 mM MgCl2 for 1 hr at 500C, and the products were separated in 5% polyacrylamide/8M urea gel in tris-borate-EDTA buffer and detected by autoradiography.

Figure 4:
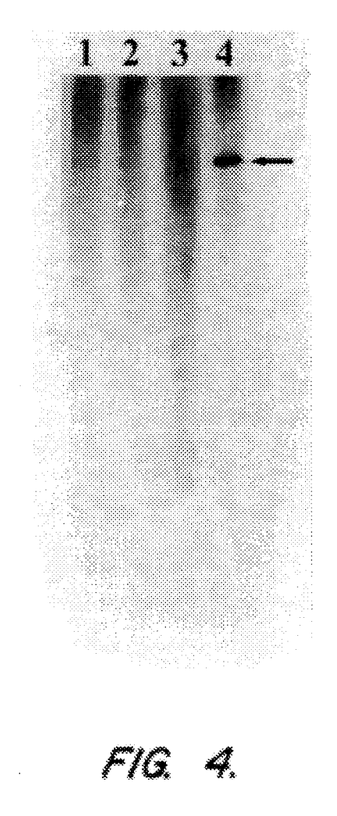

The results of the experiment are shown on FIG. 4. The ribozyme was able to effectively cleave the sense transcript, as evidenced by the appearance of an approximately 1 kb fragment, but not the anti-sense transcript of the gene. It suggests that RZ1052 has a specific catalytic activity against the UGPase mRNA and may be used to down regulate the expression of the gene.

EXAMPLE 3

Plant Transformation and Analysis of Transformants

The freeze-thaw procedure (An, *Meth. Enzymol.* 153:292–305 (1987), which is incorporated herein by reference) was used to transform *Agrobacterium tumefaciens* strain LBA4404 with recombinant plasmids. Standard transformation techniques with *Agrobacterium* strain LBA4404 were used. Virus free shoots of potato, cv. 'Russet Burbank' were obtained from the North Dakota State Seed Department. Shoot cultures were maintained by subculture of nodal cuttings on a sterile medium containing MS (Murashige and Skoog) salts, 30 g/l sucrose, 0.5 mg/l nicotinic acid, 0.5 mg/l pyridoxine HCl, 0.1 mg/l thiamine-HCl, 2.0 mg/l glycine, and 100 mg/l Myo-inositol, pH 5.6 and solidified with 2.0 g/l gelrite (Scott Laboratories Inc.). The cultures were grown in 25×150 mm glass culture tubes with translucent polypropylene caps at 23° C. with 16 hr photoperiod of 60–70 $\mu Em^{-2}s^{-1}$. Potato microtubers were initiated generally according to the method of Kwiatkowski et al., *American Potato J.* 65:369–375 (19880), which is incorporated herein by reference. The method was modified in that sucrose was increased to 100 g/l and the pH to 5.8.

After autoclaving, 0.25 mg/l ancymidol was added and 40 ml of medium were then placed in a 75×75×100 mm magenta GA-7 vessel, allowed to solidify and five individual nodes were placed in each vessel. These were then stored at 18° C. in the dark.

Transformation was performed by using a procedure based on that described in Ishida et al., *Plant Cell Rep.* 8:325–328 (1989), which is incorporated herein by reference. Briefly, freshly harvested 4–8 week old microtubers were cut into 1–2 mm discs and inoculated for 10–15 min in a rapidly growing bacterial solution containing 100 µM acetosyringone which was added 4 hr prior to inoculation. Discs were then placed on a cocultivation medium with the cut surface down. After 2 days the discs were transferred to a selection medium containing 3.5 mg/l zeatin riboside (ZR) and 0.087 mg/l indole-3-acetyl-L-aspartic acid (IAA-AA).

After 3–4 weeks the primary shoots were removed and discarded and the discs were transferred to a medium containing MS salts, 100 mg/l inositol, 0.4 mg/l thiamine HCl, 30 g/l sucrose, 3.5 mg/l ZR, 10.0 g/l gibberellic acid (GA$_3$), 2.0 g/l gelrite, 100 mg/l kanamycin and 500 mg/l carbenicillin. The secondary shoots which arose were then placed on the above medium without ZR and GA$_3$. Those that grew and produced roots on this medium were used for further analysis.

Kanamycin resistant plants were tested for the presence of the construction by polymerase chain reaction (PCR) according to standard techniques. PCR followed by blot hybridization to (β-glucuronidase) GUS or neomycin phosphtransferase (NPTII) specific probes was used. DNA from potato shoots was isolated generally by the procedure described by Shure et al. *Cell* 35:225–233 (1983), which is incorporated herein by reference. The following modifications in the procedure were made. After phenol extraction, starch and RNA were precipitated by an equal volume of 12M LiCl and pelleted by centrifugation. DNA was ethanol precipitated from the supernatant, washed with 70% ethanol and dissolved in TE (10 mM Tris-HCl pH 8.0, 1 mM EDTA).

Amplification of potato DNA was performed in Taq DNA polymerase buffer provided with the enzyme and supplemented with 1 nm/ml of each primer-oligonucleotide, 200 nM/ml of each deoxynucleotides and 1 unit of Taq DNA polymerase (Perkin Elmer) per every 50 µl of mixture. The pair of 24mer primers specific to the 5'end of the 35S promoter and to the 3'end of the NOS polyadenalation site was used. Analytical reactions were carried with 0.1µg DNA in volume 10µl and a preparative—with 2µg DNA in volume 100 µl. The reactions were performed in a Perkin-Elmer thermal cycler. The DNA was melted at 94° C. for 5 min during the first cycle and for 1 min during each subsequent cycle. Annealing was performed at 55° C. for 1 min and the polymerization at 72° C. for 2 min during the cycle. A total of 35 cycles was used to obtain the product.

The site-specific priming allowed amplification of the region containing GUS with the antisense gene and generated a 3.2 kb fragment. Kanamycin resistance in combination with PCR analysis suggested that the entire cassette was successfully transferred from Agrobacterium into the plant cell. About 25% (64 out of 262) of all the kanamycin resistant plants were positive in PCR test. About 10% (8 out of 64) of those plants generated an incorrectly sized fragment. The rest of the kanamycin resistant plants did not produce any PCR product. Only the kanamycin resistant plants generating the correctly sized PCR product were used for further analysis.

In addition, inverse PCR was used to estimate the number of integrated copies per genome. The reaction was carried by the of method Does et al., *Plant Mol. Biol.* 17:151–153 (1991), which is incorporated herein by reference. The results showed the presence of a single copy of the insert in most transgenic plants (Table 1). Without relation to copy number some plants were weaker then others. In addition, some were not able to form roots. All rescued transgenic plants were healthy after transfer to the greenhouse.

TABLE 1

UGPase activity in stem samples of tissue grown transgenic Russet Burbank potatoes.

| Plant # | Construction | Copy [1] | UGPase Activity[2] | % Control[3] |
|---|---|---|---|---|
| Control | — | — | 2.81 ± 0.06 | 100 |
| 1809 | RZ | 1 | 1.48 ± 0.30 | 53* |
| 1400 | AS | 1 | 1.87 ± 0.09 | 67* |
| 1653 | RZ | 1 | 1.98 ± 0.10 | 70* |
| 1521 | RZ | 1 | 2.17 ± 0.03 | 77* |
| 1685 | AS | 1 | 2.17 ± 0.37 | 77* |
| 1621 | AS | 1 | 2.29 ± 0.18 | 81* |
| 1804 | AS | 1 | 2.34 ± 0.18 | 83* |
| 1277 | AS | 2 | 2.41 ± 0.03 | 86* |
| 1796 | RZ | 1 | 2.43 ± 0.14 | 86* |
| 685 | AS | 2 | 2.47 ± 0.04 | 88* |
| 1563 | AS | 1 | 2.48 ± 0.06 | 88* |
| 1666 | AS | 1 | 2.48 ± 0.08 | 88* |
| 1511 | AS | 1 | 2.54 ± 0.02 | 90* |
| 1454 | AS | 1 | 2.55 ± 0.05 | 91* |
| 1807 | RZ | 2 | 2.56 ± 0.09 | 91* |
| 1834 | AS | 1 | 2.57 ± 0.05 | 91* |
| 1682 | AS | 2 | 2.63 ± 0.06 | 94* |
| 1622 | RZ | 1 | 2.65 ± 0.02 | 94* |
| 1449 | AS | 1 | 2.76 ± 0.09 | 98 |
| 1665 | RZ | 1 | 2.77 ± 0.03 | 99 |
| 1570 | RZ | 2 | 2.77 ± 0.05 | 99 |
| 1642 | RZ | 3 | 2.84 ± 0.08 | 101 |
| 1291 | AS | 1 | 2.86 ± 0.05 | 102 |

[1] minimum copy number.
[2] UGPase activity is expressed as units per mg protein.
[3] If the % control value is followed by an * symbol, the standard error of the activity for the control and the transgenic plant to not overlap.

TABLE 2

UGPase activity in tubers of greenhouse grown transgenic Russet Burbank potatoes.

| Plant # | Construction | Copy # | UGPase Activity[1] | % Control[2] |
|---|---|---|---|---|
| Control | — | — | 4.96 ± 0.30 | 100 |
| 1400 | AS | 1 | 3.29 ± 0.60 | 66* |
| 685 | AS | 2 | 3.36 ± 0.19 | 68* |
| 1291 | AS | 1 | 4.42 ± 0.07 | 89* |
| 1521 | RZ | 1 | 4.56 ± 0.36 | 92 |
| 1685 | AS | 1 | 4.58 ± 0.09 | 92 |
| 1277 | AS | 2 | 4.91 ± 0.09 | 99 |
| 1511 | AS | 1 | 5.05 ± 0.13 | 102 |
| 1682 | AS | 2 | 5.16 ± 0.32 | 104 |

[1] UGPase activity is expressed as units per mg protein.
[2] If the % control value is followed by an * symbol, the standard error of the activity for the control and the transgenic plant do not overlap.

UGPase activity was assayed in stem and tuber extracts using the one-step method of Sowokinos, *Plant Physiol.* 57:63–68 (1976), which is incorporated herein by reference. The UGPase activity in stems of tissue-culture-grown transgenic plants and tubers of greenhouse-grown plants exhibited a wide range of activity from 53% to 102% of the activity of control plants (Tables 1 and 2). Three of the five transformants with the lowest activities contained the ribozyme constructs. These results show that ribozymes are effective in controlling gene expression in transgenic plants.

The maximum reduction of UGPase activity was 53% of the control. Because sucrose is the primary source of carbon to the growing plant, down regulating the expression of UGPase to lower levels may prevent the regeneration of functional plants. Circumstantial evidence supports this concept. Several shoots selected in the presence of kanamycin grew normally in kanamycin-containing rooting media, but did not develop roots. These non-rooting plants were screened and were positive for the integration of the transgene. Several of these plants have been rescued and are now rooting in the absence of kanamycin. One possible explanation for the non-rooting phenotype is that these plants may have a higher level of down regulation of UGPase activity which limited sucrose availability to developing roots.

The results described in the Examples, above, demonstrate the ability of the antisense and ribozymes constructs of the present invention to inhibit UGPase activity in transgenic plants. Although the invention has been described in some detail in these examples for purposes of clarity and understanding, it will be apparent that certain changes and modifications may be practiced within the scope of the appended claims.

What is claimed is:

1. A method of inhibiting accumulation of hexose sugars in a potato plant, the method comprising introducing into the potato plant an expression cassette comprising a promoter sequence operably linked to a polynucleotide sequence from a potato gene encoding UDP-glucose pyrophosphorylase in an antisense orientation such that transcription of the polynucleotide sequence inhibits expression of an endogenous UDP-glucose pyrophosphorylase gene and accumulation of hexose sugars is inhibited.

2. The method of claim 1, wherein the plant is *Solanum tuberosum*.

3. The method of claim 1, wherein the polynucleotide sequence is contained within a nucleotide sequence encoding a ribozyme specific to UDP-glucose pyrophosphorylase mRNA.

4. The method of claim 1, wherein the polynucleotide sequence consists essentially of between 50 and about 2000 basepairs.

5. The method of claim 1, wherein the polynucleotide sequence consists essentially of 1.2 kb from the gene.

6. The method of claim 1, wherein the promoter is constitutive.

7. The method of claim 6, wherein the promoter is a 35S promoter of cauliflower mosaic virus.

8. The method of claim 1, wherein the expression cassette is introduced into the plant using *Agrobacterium*.

9. A potato plant comprising an expression cassette comprising a promoter sequence operably linked to a polynucleotide sequence from a potato gene encoding UDP-glucose pyrophosphorylase, wherein the polynucleotide sequence is linked to the promoter sequence in an antisense orientation.

10. The plant of claim 9, wherein the polynucleotide sequence is contained within a nucleotide sequence encoding a ribozyme specific to UDP-glucose pyrophosphorylase mRNA.

11. The plant of claim 9, wherein the polynucleotide sequence consists essentially of between 50 basepairs and about 2000 base pairs.

12. A recombinant expression cassette comprising a plant promoter sequence operably linked to a polynucleotide sequence from a potato gene encoding UDP-glucose pyrophosphorylase, wherein the polynucleotide sequence is linked to the promoter sequence in an antisense orientation.

13. The recombinant expression cassette of claim 12, wherein the polynucleotide sequence is contained within a nucleotide sequence encoding a ribozyme specific to UDP-glucose pyrophosphorylase mRNA.

14. The recombinant expression cassette of claim 12, wherein the polynucleotide sequence consists essentially of between 50 and about 2000 basepairs.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( v i ) ORIGINAL SOURCE:
        ( A ) ORGANISM: Solanum tuberosum     ( x i ) SEQUENCE DESCRIPTION: SEQ ID NO:1:

Trp Tyr Pro Pro Gly His Gly
        1                     5

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( v i ) ORIGINAL SOURCE:
        ( A ) ORGANISM: Solanum tuberosum     ( i x ) FEATURE:
        ( A ) NAME/KEY: modified_base (B) LOCATION: 9
(D) OTHER INFORMATION: /mod_base=i (ix) FEATURE:
(A) NAME/KEY: modified_base
(B) LOCATION: 12
(D) OTHER INFORMATION: /mod_base=i (ix) FEATURE:
(A) NAME/KEY: modified_base
(B) LOCATION: 15
(D) OTHER INFORMATION: /mod_base=i (xi) SEQUENCE DESCRIPTION: SEQ ID NO:2:

TGGTA Y CCNC CNGGNCA Y GG                    20

(2) INFORMATION FOR SEQ ID NO:3:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (iii) HYPOTHETICAL: NO (vi) ORIGINAL SOURCE:
(A) ORGANISM: Solanum tuberosum (xi) SEQUENCE DESCRIPTION: SEQ ID NO:3:

Thr  Gly  Asp  Val  Trp  Phe  Gly
 1                  5

(2) INFORMATION FOR SEQ ID NO:4:

(i) SEQUENCE CHARACTERISTICS:
(A) LENGTH: 20 base pairs
(B) TYPE: nucleic acid
(C) STRANDEDNESS: single
(D) TOPOLOGY: linear (vi) ORIGINAL SOURCE:
(A) ORGANISM: Solanum Tuberosum (ix) FEATURE:
(A) NAME/KEY: modified_base
(B) LOCATION: 3
(D) OTHER INFORMATION: /mod_base=i (ix) FEATURE:
(A) NAME/KEY: modified_base
(B) LOCATION: 6
(D) OTHER INFORMATION: /mod_base=i (ix) FEATURE:
(A) NAME/KEY: modified_base
(B) LOCATION: 12
(D) OTHER INFORMATION: /mod_base=i (xi) SEQUENCE DESCRIPTION: SEQ ID NO:4:

TGNCCNCTAC ANACCAARCC                        20

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (iii) HYPOTHETICAL: NO (v i) ORIGINAL SOURCE:
    (A) ORGANISM: Solanum tuberosum (x i) SEQUENCE DESCRIPTION: SEQ ID NO:5:

TCTAGAGGAT CCCCGGG                                                               17

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i i) HYPOTHETICAL: NO (v i) ORIGINAL SOURCE:
        (A) ORGANISM: Solanum tuberosum (x i) SEQUENCE DESCRIPTION: SEQ ID NO:6:

AAACCCGGCC AGGTCGAATC CATCCAA                                                    27

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i i) HYPOTHETICAL: NO (v i) ORIGINAL SOURCE:
        (A) ORGANISM: Solanum tuberosum (x i) SEQUENCE DESCRIPTION: SEQ ID NO:7:

CATGGGCCGG TCCAAAGCAG GAGTGCCTGA GTAGTCCTTA GGTAGATC                             48